United States Patent [19]

Lang et al.

[11] Patent Number: 5,064,641
[45] Date of Patent: Nov. 12, 1991

[54] POLYVALENT METAL SALTS OF SULPHONTED DERIVATIVES OF BENZYLIDENECAMPHOR AND THEIR USE FOR PROTECTING THE SKIN AGAINST ULTRAVIOLET RADIATION

[75] Inventors: Gerard Lang, Saint-Gratien; Serge Forestier, Claye-Souilly; Claudine Morie, Aulnay-sous-Bois; Alain Lagrange, Chatou, all of France

[73] Assignee: L'Oreal, Paris, France

[21] Appl. No.: 439,977

[22] Filed: Nov. 22, 1989

[30] Foreign Application Priority Data

Nov. 22, 1988 [LU] Luxembourg ............ 87.394

[51] Int. Cl.$^5$ .............. A61K 7/44; C07C 309/19; C07F 7/00; C07F 9/80
[52] U.S. Cl. ............... 424/60; 562/100; 556/120; 556/54; 556/27
[58] Field of Search ............ 562/100; 556/54, 27, 556/120; 424/60

[56] References Cited

U.S. PATENT DOCUMENTS

| | | | |
|---|---|---|---|
| 4,165,336 | 8/1978 | Bouillon et al. | 562/100 |
| 4,250,108 | 2/1981 | Bouillon et al. | 562/100 |
| 4,304,730 | 12/1981 | Bouillon et al. | 562/100 |
| 4,323,549 | 4/1982 | Bouillon et al. | 424/45 |
| 4,327,031 | 4/1982 | Bouillon et al. | 562/100 |
| 4,330,488 | 5/1982 | Bouillon et al. | 562/100 |
| 4,421,739 | 12/1983 | Bouillon et al. | 562/100 |
| 4,585,597 | 4/1986 | Lang et al. | |
| 4,654,434 | 3/1987 | Lang et al. | 560/51 |
| 4,663,088 | 5/1987 | Lang et al. | 562/100 |

FOREIGN PATENT DOCUMENTS 2236515 2/1975 France .
2383904 10/1978 France .
2528420 12/1983 France .

OTHER PUBLICATIONS

Liem et al., Intern. J. Cosmetic Science, 1, 341-361 (1979).

Primary Examiner—Nicky Chan
Attorney, Agent, or Firm—Fleit, Jacobson, Cohn, Price, Holman & Stern

[57] ABSTRACT

Polyvalent metal salt of a sulphonated derivative of benzylidenecamphor having the general formula:

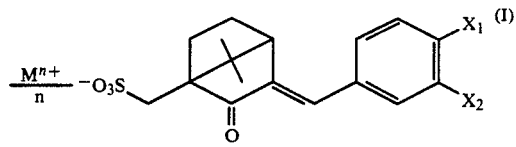

in which $M^{n+}$ denotes a polyvalent metal cation in which n is equal to 2, 3 or 4; and One of the symbols $X_1$ or $X_2$ denotes a hydrogen atom, the other denoting one of the following radicals $Y_1$ $Y_2$:

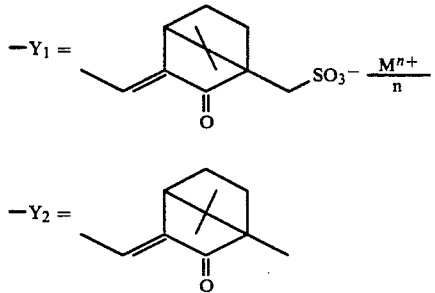

where $M^{n+}$ has the same meaning as above.

Cosmetic composition screening out UV rays of wavelengths 280-380 nm, containing the compound of formula (I) as well as, optionally, other sunscreens.

13 Claims, No Drawings

POLYVALENT METAL SALTS OF SULPHONTED DERIVATIVES OF BENZYLIDENECAMPHOR AND THEIR USE FOR PROTECTING THE SKIN AGAINST ULTRAVIOLET RADIATION

The present invention relates to new polyvalent metal salts of sulphonated derivatives of benzylidenecamphor and to their use as sunscreens in cosmetic compositions.

It is known that light radiation of wavelengths between 280 and 400 nm permit tanning of the human epidermis and that rays of wavelengths between 280 and 320 nm, known by the name of "UV-B", also cause erythema and skin burns which can impair the development of the tan.

The use of compounds active in the abovementioned wavelength range 280-320 nm is already known. French Patents Nos. 2,282,426 and 2,236,515 described, for example, polyvalent metal salts of benzylidenecamphor derivatives sulphonated on the methyl radical at the 10-position of the camphor or at the 3'- or 4'-position on the benzene ring.

However, while UV-B rays of wavelengths between 280 and 320 nm play a predominant part in the production of solar erythema and must be screened out, it is nonetheless true that UV-A rays of wavelengths between 320 and 400 nm, causing tanning of the skin, also cause deterioration of the latter, in particular in the case of sensitive skin or skin continually exposed to solar radiation. It has been found that UV-A rays can enhance the action of UV-B rays. UV-A rays promote triggering of the erythemal reaction, or accentuate this reaction in some subjects. Similarly, they can be the source of phototoxic or photoallergic reactions.

Accordingly, compounds have been sought which are capable of absorbing both UV-A rays and UV-B rays harmful to the skin, and of having the capacity to protect products sensitive to these types of radiation.

French Patent No. 2,528,420 describes such compounds, consisting of water-soluble alkali metal or amine salts of benzylidenecamphor derivatives sulphonated at the 10-position of the camphor.

Unfortunately, all these polyvalent metal or alkali metal salts of benzylidenecamphor derivatives of the prior art have a relatively low absorbing power when used at low concentration. To obtain high protection, it is hence necessary either to increase their concentration or to add other screening agents or alternatively pigments such as titanium oxide.

In point of fact, it is known that agents screening out UV rays can cause adverse side effects, and that it is in the interest of the cosmetologist to obtain the desired index of protection with the smallest possible amount of screening agents in the composition.

Moreover, when a pigment is used, a cosmetic composition is obtained which has good screening power, but which leaves a whiteish film, dislike by the users, remaining on the skin after application.

Apart from a high index of protection and an attractive appearance when applied, a cosmetic screening composition is also required not to be sticky to the touch and to show good chemical and photochemical stability and also great persistence.

Persistence may be defined as the stability of the index of protection of the screening composition during exposure of the subject to the sun. It is important that this persistence is high, since the index of protection must be constant during exposure, thereby avoiding repeated applications at regular and frequent intervals in order to obtain effective protection of the skin against UV rays.

This index of protection can vary either because the screening agent is photochemically unstable, or because it penetrates into the skin and no longer performs its function, or alternatively because it becomes removed during bathing.

The Applicant discovered that a particular family of polyvalent metal salts of sulphonated derivatives of benzylidenecamphor, constituting water-insoluble pigments, made it possible to meet all these requirements and to obtain, in particular, excellent protection with respect to ultraviolet radiation, even at low concentration. The water-insolubility of these compounds contributes, moreover, to the provision of great persistence of this protection, even after prolonged bathing.

The subject of the present invention is hence new polyvalent metal salts of sulphonated derivatives of benzylidenecamphor, corresponding to the following general formula:

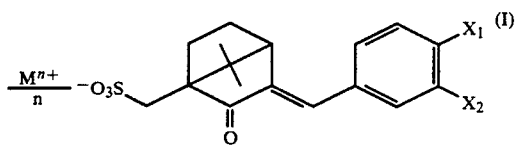

in which $M^{n+}$ denotes a polyvalent metal cation in which n is equal to 2, 3 or 4; $M^{n+}$ preferably denotes $Ca^{2+}$, $Zn^{2+}$, $Mg^{2+}$, $Ba^{2+}$ $Al^{3+}$ or $Zr^{4+}$; and one of the symbols $X_1$ or $X_2$ denotes a hydrogen atom, the other denoting one of the following radicals $Y_1$ or $Y_2$:

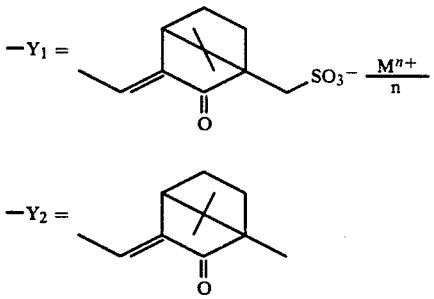

$M^{n+}$ having the same meaning as above.

The compounds (1) according to the invention are water-insoluble but readily redispersible in an aqueous medium.

By way of especially preferred compounds, the compounds of formula (I) in which $M^{n+}$ denotes $Ca^{2+}$, $Zn^{2+}$, $Mg^{2+}$, $Al^{3+}$ or $Zr^{4+}$, $X_2$ denotes a hydrogen atom and $X_1$ denotes a radical $Y_1$ or $Y_2$ may be mentioned.

The compounds of general formula (I) may be prepared by adding a polyvalent metal salt or hydroxide of formula (II), optionally in aqueous suspension or solution

to an aqueous solution of a benzylidenecamphor derivative of formula (III)

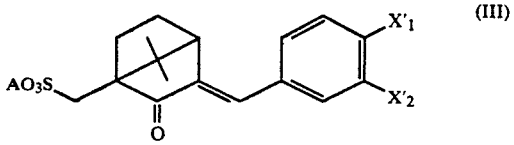

In the compound (II), Z denotes an inorganic or organic anion, m is equal to 1 or 2 and n has the value stated above. Among anions, there may be mentioned halide anions, especially bromide and chloride, and nitrate, acetate and hydroxyl anions for monovalent anions, and carbonate and sulphate anions for divalent anions.

In the compound of formula (III),

A denotes a hydrogen atom, an alkali metal such as sodium or potassium or an ammonium residue, and one of the symbols $X'_1$ or $X'_2$ denotes a hydrogen atom, the other denoting one of the following radicals $Y'_1$ or $Y'_2$:

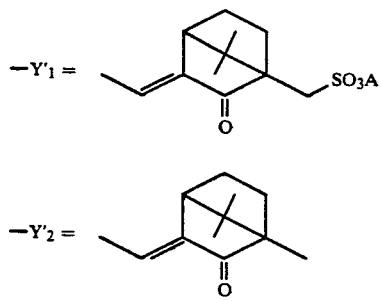

where A has the same meaning as above.

The addition of the polyvalent metal salt is performed with stirring. When the compound of formula (III) is in the form of a sulphonic acid, the pH of the reaction mixture may be adjusted, if appropriate, to around neutrality during the reaction by adding an aqueous solution of an alkali metal hydroxide or of ammonium hydroxide.

This reaction may also be carried out by reversing the order of introduction of the reactants.

The polyvalent metal salt (II) is preferably used in a stoichiometric amount of salify the compound of formula (III).

The compound of formula (I) precipitates during the reaction. It is isolated by filtration and then washed with water to remove the inorganic salts.

The compounds of formula (III) are known, and may be prepared according to the procedures described in French Patent 2,528,420.

It should be understood that the compounds of formula (I) or (III) can give rise to "cis-trans" isomerism around one or more double bond(s), and that all the isomers form part of the invention.

The subject of the present invention is also a cosmetic composition screening out UV rays in the wavelength range extending from 280 to 380 nm, containing, as a protective agent against ultraviolet rays, an effective amount of at least one polyvalent metal salt of a sulphonated derivative of benzylidenecamphor of formula (I) according to the invention, in a cosmetically acceptable medium.

When used as a composition intended for protection of the human epidermis against ultraviolet rays, the cosmetic composition according to the invention may be presented in the most varied forms customarily used for this type of composition. It is presented, in particular, in the form of a suspension, emulsion such as a cream or milk, gel, solid stick or powder, or is packaged as an aerosol.

It can contain cosmetic adjuvants customarily used in this type of composition, such as thickeners, emollients, humectants, surfactants, preservatives, antifoams, fragrences, oils, waxes, lanolin, propellants, colourings and/or pigments whose function is to colour the composition itself or the skin, or any other ingredient customarily used in cosmetics.

The compound of formula (I) is present in proportions of between 0.25 and 3% by weight relative to the total weight of the composition.

The present invention also relates to cosmetic antisun compositions containing at least one compound of formula (I), which may be combined with other sunscreens specific for UV-B and/or UV-A radiation and compatible with the compound (I) according to the invention. In this case, the concentration of the compound of formula (I) is between 0.5 and 10%, and the total concentration of sunscreens is between 0.5 and 15% by weight relative to the total weight of the composition.

The subject of the invention is also a process for protecting the human epidermis against UV-A rays and UV-B rays consisting in applying to the skin an effective amount of at least one compound of formula (I) contained in a cosmetically acceptable medium, optionally in combination with other agents absorbing UV-A or UV-B rays.

The invention is illustrated by the non-limiting examples below.

PREPARATION EXAMPLES

EXAMPLE 1

Preparation of a compound of general formula (I) in which $M^{n+}$ denotes $Mg^{2+}$, $X_2$ is a radical $Y_1$ and $X_2$ is a hydrogen atom 3 litres of water are added to 1 kg of a 30% aqueous solution of terephthalylidenedicamphorsulphonic acid (0.533 mole). 108 g (0.533 mole) of magnesium chloride hexahydrate are introduced with stirring, and stirring is maintained for 90 minutes.

The reaction mixture is filtered. The white solid obtained is washed with water while stirring and then with ethanol, and dried under reduced pressure.

260 g of expected product are thereby obtained in the form of a white powder possessing the following characteristics:

Melting point: >300° C.

| Elemental analysis: $C_{28}H_{32}O_8S_2Mg.5H_2O$ | | | | |
|---|---|---|---|---|
| | C % | H % | O % | S % | Mg % |
| Calculated: | 49.81 | 6.27 | 30.81 | 9.49 | 3.60 |
| Found: | 51.14 | 6.57 | 29.51 | 8.67 | 4.11 |

EXAMPLE 2

Preparation of a compound of general formula (I) in which $M^{n+}$ denotes $Zn^{2+}$, $X_1$ is a radical $Y_1$ and $X_2$ is a hydrogen atom 700 cm³ of water are added to 200 g of a 29.5% aqueous solution of terephthalylidenedicamphorsulphonic acid (0.105 mole). 14.2 g (0.105 mole) of zinc chloride dihydrate, dissolved in 160 cm³ of water, are introduced with stirring, and stirring is maintained for 3 hours.

The reaction mixture is filtered. The white solid is washed with water while stirring and dried under reduced pressure.

57 g of expected product are thereby obtained in the form of a white powder possessing the following characteristics:

Melting point: >300° C.

| Elemental analysis: $C_{28}H_{32}O_8S_2Zn.6H_2O$ | | | | | |
|---|---|---|---|---|---|
| | C % | H % | O % | S % | Zn % |
| Calculated: | 45.78 | 5.99 | 30.52 | 8.72 | 8.86 |
| Found: | 45.30 | 6.03 | 31.09 | 8.68 | 9.11 |

EXAMPLE 3

Preparation of a compound of general formula (I) in which $M^{n+}$ denotes $Al^{3+}$, $X_1$ is a radical $Y_1$ and $X_2$ is a hydrogen atom 30 cm³ of water are added to 30 g of a 29.5% aqueous solution of terephthalylidenedicamphorsulphonic acid (0.016 mole). 2.41 g (0.013 mole) of aluminum chloride trihydrate, dissolved in 10 cm³ of water, are introduced with stirring, 50 cm³ of water are added and stirring is maintained for 3 hours.

The reaction mixture is filtered. The white solid obtained is washed with water while stirring and dried under reduced pressure.

8.4 g of expected product are thereby obtained in the form of a white powder possessing the following characteristics:

Melting point: >300° C.

| Elemental analysis: $C_{84}H_{95}O_{24}S_6Al_2.22H_2O$ | | | | | |
|---|---|---|---|---|---|
| | C % | H % | O % | S % | Al % |
| Calculated: | 47.28 | 6.57 | 34.50 | 9.00 | 2.53 |
| Found: | 46.71 | 6.46 | 31.96 | 8.84 | 2.43 |

EXAMPLE 4

Preparation of a compound of general formula (I) in which $M^{n+}$ denotes $Ca^{2+}$, $X_1$ is a radical $Y_2$ and $X_2$ is a hydrogen atom 4.82 g (0.01 mole) of terephthalylidene(camphor) (camphorsulphonic acid) are dissolved in 100 cm³ of water. 0.735 g (0.005 mole) of calcium chloride dihydrate, dissolved in 10 cm³ of water, are introduced with stirring, and stirring is maintained for 2 hours.

The reaction mixture is filtered. The white solid obtained is washed with water while stirring and dried under reduced pressure.

4.6 g of expected product are thereby obtained in the form of a white powder possessing the following characteristics:

Melting point: >300° C.

| Elemental analysis: $C_{56}H_{65}O_{10}S_2Ca.4H_2O$ | | | | | |
|---|---|---|---|---|---|
| | C % | H % | O % | S % | Ca % |
| Calculated: | 62.51 | 6.88 | 20.84 | 5.95 | 3.72 |
| Found: | 62.80 | 6.86 | 20.79 | 5.85 | 3.67 |

EXAMPLE 5

Preparation of a compound of general formula (I) in which $M^{n+}$ denotes $Ca^{2+}$, $X_1$ is a radical $Y_1$ and $X_2$ is a hydrogen atom 100 cm³ of water are added to 100 g of a 29.5% aqueous solution of terephthalylidenedicamphorsulphonic acid (0.0525 mole). 7.7 g (0.0525 mole) of calcium chloride dihydrate, dissolved in 50 cm³ of water, are introduced with stirring, and stirring is maintained for 1 hour.

The reaction mixture is filtered. The white solid obtained is washed with stirring and dried under reduced pressure.

27 g of expected product are thereby obtained in the form of a white powder possessing the following characteristics:

Melting point: >300° C.

| Elemental analysis: $C_{28}H_{32}O_8S_2Ca.4H_2O$ | | | | | |
|---|---|---|---|---|---|
| | C % | H % | O % | S % | Ca % |
| Calculated: | 49.92 | 5.94 | 28.53 | 9.50 | 5.94 |
| Found: | 49.61 | 5.99 | 29.06 | 8.90 | 6.44 |

EXAMPLE 6

Preparation of a compound of general formula (I) in which $M^{n+}$ denotes $Zr^{4+}$, $X_1$ is a radical $Y_1$ and $X_2$ is a hydrogen atom 750 cm³ of water are added to 200 g of a 30% aqueous solution of terephthalylidenedicamphorsulphonic acid (0.106 mole).

12.3 g (0.053 mole) of anhydrous zirconium chloride, dissolved in 925 cm³ of water, are introduced with stirring, and stirring is maintained for 1 hour.

The reaction mixture is filtered. The white solid is washed with water and then dried under reduced pressure.

46.1 g of product are obtained in the form of a white powder having the following characteristics:

Melting point: >250° C.

Weight ratio carbon/sulfur in the compound $C_{56}H_{64}O_{16}S_4Zr$

| | |
|---|---|
| Calculated: | 5.25 |
| Found: | 5.20 |

FORMULATION EXAMPLES

EXAMPLE A

| O/W antisun milk | |
|---|---|
| Compound of Example 1 | 2.0 g |
| 2-Ethylhexyl para-methoxycinnamate | 3.0 g |
| Oleocetyl alcohol containing 30 moles of ethylene oxide | 6.0 g |
| Stearyl alcohol | 4.0 g |
| Benzoate of $C_{12}$-$C_{15}$ alcohols, sold by the company FINETEX under the name "FINSOLV TN" | 13.0 g |
| Sorbitol, 70% | 16.0 g |
| Preservative | qs |
| Fragrance | qs |
| Triethanolamine | qs pH: 7.0 |
| Demineralized water | qs 100.0 g |

The 2-ethylhexyl p-methoxycinnamate is dissolved in the fatty phase, which is heated to about 70°–75° C. The compound of Example 1 is dispersed in the aqueous phase, which is heated to about 70°–75° C.

With brisk stirring, the fatty phase is added to the aqueous phase; the mixture is then left to cool with moderate stirring. At about 40° C., the fragrance and the preservative are added.

EXAMPLE B

| W/O antisun cream | |
|---|---|
| Compound of Example 5 | 2.5 g |
| Compound of Example 2 | 1.5 g |
| 2-Ethylhexyl para-dimethylaminobenzoate | 6.0 g |
| Magnesium stearate | 3.5 g |
| Hydrogenated lanolin, sold by the company ONYX under the name "HYDROLAN H" | 1.5 g |
| Clear lanolin | 4.0 g |
| Beeswax | 4.5 g |
| Sorbitan sesquioleate | 4.5 g |
| Liquid paraffin | 20.0 g |
| Octyldodecanol | 10.0 g |
| Preservative | qs |
| Fragrance | qs |
| Triethanolamine | qs pH: 6.0 |
| Demineralized water | qs 100.0 g |

The 2-ethylhexyl para-dimethylaminobenzoate is dissolved in the fatty phase containing the emulsifier. The compounds of Examples 2 and 5 are dispersed in the aqueous phase.

The two phases are heated to 70°–75° C. and, with brisk stirring, the aqueous phase is added to the fatty phase. The mixture is left to cool with moderate stirring and, at 40° C., the fragrance and the preservative are added.

EXAMPLE C

| Thickened antisun oil | |
|---|---|
| Compound of Example 3 | 3.0 g |
| 2-Ethylhexyl para-methoxycinnamate | 2.5 g |
| 2-Ethylhexyl para-dimethylaminobenzoate | 1.5 g |
| Rapeseed oil | 30.0 g |
| Silica sold by the company DEGUSSA under the name "AEROSIL R972" | 7.0 g |
| Tetracyclodimethylsiloxane | 10.0 g |
| tert-Butyl-para-cresol | 0.1 g |
| Fragrance | qs |
| Isopropyl myristate | qs 100.0 g |

The compound of Example 3 is dispersed in the fatty phase containing the screening agents, and the silica is added.

EXAMPLE D

| Antisun O/W emulsion | |
|---|---|
| Compound of Example 2 | 5.0 g |
| Cetyl/stearyl alcohol | 1.6 g |
| Cetyl/stearyl alcohol containing 33 moles of ethylene oxide | 6.4 g |
| Mixture of glycerol mono- and distearates, sold by the company GATTEFOSSE under the name "GELEOL" | 3.5 g |
| Liquid paraffin | 15.0 g |
| Propylene glycol | 5.0 g |
| Glycerol | 15.0 g |
| Preservative | qs |
| Fragrance | qs |
| Triethanolamine | qs pH: 7.0 |

| Antisun O/W emulsion | |
|---|---|
| Demineralized water | qs 100.0 g |

The fatty phase is heated to 70°–75° C. The compound of Example 2 is dispersed in the aqueous phase, which is heated to the same temperature.

With brisk stirring, the fatty phase is added to the aqueous phase, and the mixture is then left to cool with moderate stirring. At about 40° C., the fragrance and preservative are added.

EXAMPLE E

| Aqueous antisun gel | |
|---|---|
| Compound of Example 2 | 2.0 g |
| 2-Hydroxy-4-methoxybenzophenone | 0.3 g |
| Propylene glycol | 15.0 g |
| Ehtyl alcohol | 5.0 g |
| Carboxyvinyl polymer, sold by the company GOODRICH CHEMICAL under the name "CARBOPOL 940" | 0.4 g |
| Preservative | qs |
| Fragrance | qs |
| Triethanolamine | qs pH: 6.5 |
| Demineralized water | qs 100.0 g |

The compound of Example 2 is dispersed in the aqueous-alcoholic medium containing the 2-hydroxy-4-methoxybenzophenone; the Carbopol is added and finally the triethanolamine, the preservative and the fragrance.

EXAMPLE F

| Antisun O/W emulsion | |
|---|---|
| Compound of Example 3 | 1.5 g |
| Compound of Example 5 | 1.5 g |
| 2-Phenylbenzimidazole-5-sulphonic acid | 3.0 g |
| 50:50 mixture of glycerol monostearate and polyethylene glycol stearate containing 100 moles of ethylene oxide, sold by the company SEPPIC under the name "SIMULSOL 165" | 8.0 g |
| Stearyl alcohol | 6.0 g |
| Liquid paraffin | 20.0 g |
| Glycerol | 10.0 g |
| Preservative | qs |
| Fragrance | qs |
| Sodium hydroxide | qs pH: 7.0 |
| Demineralized water | qs 100.0 g |

The fatty phase is heated to about 70°–75° C. The compounds of Examples 3 and 5 are dispersed in the aqueous phase containing the 2-phenylbenzimidazole-5-sulphonic acid, this phase being heated to about 70°–75° C.

With brisk stirring, the fatty phase is added to the aqueous phase, and the mixture is then left to cool with moderate stirring. At about 40° C., the fragrance and preservative are added.

EXAMPLE G

| Anhydrous makeup foundation | |
|---|---|
| Compound of Example 1 | 2.0 g |
| Candelilla wax | 2.0 g |
| Ozokerite | 2.0 g |
| Lanolin alcohols | 2.0 g |
| Vaseline | 12.0 g |

-continued

| Anhydrous makeup foundation | |
| --- | --- |
| Isopropyl myristate | 10.0 g |
| Isopropyl stearate | 13.0 g |
| Sunflower oil | 13.0 g |
| Isotridecyl isononanoate | 20.0 g |
| Butylated hydroxytoluene | 0.1 g |
| Talc | 7.0 g |
| Magnesium carbonate | 8.0 g |
| Titanium oxide | 7.0 g |
| Yellow iron oxide | 1.1 g |
| Red iron oxide | 0.7 g |
| Black iron oxide | 0.1 g |
| | 100.0 g |

EXAMPLE H

| Face powder | |
| --- | --- |
| Compound of Example 2 | 1.0 g |
| Mica | 20.0 g |
| Talc | 30.0 g |
| Modified rice starch | 30.0 g |
| Kaolin | 30.0 g |
| Zinc stearate | 2.0 g |
| Red iron oxide | 0.5 g |
| Yellow iron oxide | 0.8 g |
| Black iron oxide | 0.1 g |
| Nylon powder | 8.8 g |
| Liquid paraffin | 3.0 g |
| Fragrance | 0.8 g |
| Magnesium carbonate | 1.0 g |
| | 100.0 g |

We claim:

1. A polyvalent metal salt of a sulphonated derivative of benzylidene camphor of formula (I):

$$\frac{M^{n+}}{n} -O_3S \text{—[structure]—} \begin{matrix} X_1 \\ X_2 \end{matrix} \quad (I)$$

wherein $M^{n+}$ is a polyvalent metal cation in which n is 2, 3, or 4; one of $X_1$ and $X_2$ is hydrogen and the other is $Y_1$ or $Y_2$;

$$Y_1 = \text{[structure]} -SO_3^- \frac{M^{n+}}{n}$$

$$Y_2 = \text{[structure]};$$

and said salts are insoluble in water.

2. The compound of claim 1, wherein $M^{n+}$ is selected from the group consisting of $Ca^{2+}$, $Zn^{2+}$, $Mg^{2+}$, $Ba^{2+}$, $Al^{3+}$, and $Zr^{4+}$.

3. The compound of claim 1, wherein $X_2$ is hydrogen.

4. The compound of claim 2, wherein $M^{n+}$ is selected from the group consisting of $Ca^{2+}$, $Zn^{2+}$, $Mg^{2+}$, $Al^{3+}$, and $Zr^{4+}$, and $X_2$ is hydrogen.

5. A cosmetic composition for screening out ultraviolet (UV) rays that have wavelengths between 280 and 380 nm, comprising, in a cosmetically acceptable medium, an effective concentration of at least one compound of claim 1, wherein said amount is effective for screening out UV rays that have wavelengths between 280 and 380 nm.

6. The cosmetic composition of claim 5, wherein in at least one of said compounds of formula (I) $M^{n+}$ is selected from the group consisting of $Ca^{2+}$, $Zn^{2+}$, $Mg^{2+}$, $Ba^{2+}$, $Al^{3+}$, and $Zr^{4+}$.

7. The cosmetic composition of claim 6, wherein $M^{n+}$ is selected from the group consisting of $Ca^{2+}$, $Zn^{2+}$, $Mg^{2+}$, $Al^{3+}$, and $Zr^{4+}$ and $X_2$ is hydrogen.

8. The cosmetic composition of claim 5, which is in the form of a suspension, emulsion, gel, solid stick, powder or aerosol.

9. The cosmetic composition of claim 5, further comprising at least one cosmetic adjuvant selected form the group consisting of thickeners, emollients, humectants, surfactants, preservatives, antifoams, fragrances, oils, waxes, lanolin, propellants, colorings, and pigments.

10. The cosmetic composition of claim 6, wherein said composition is in the form of a protective composition for the human epidermis and said effective concentration is between 0.25 and 3% by weight relative to the total weight of the composition.

11. The cosmetic composition of claim 5, further comprising sunscreens, other than compounds of formula (I), that are effective for screening out UV-A or UV-B rays.

12. The cosmetic composition of claim 11, wherein the concentration of compounds of formula (I) is from 0.5 to 10% by weight and the total concentration of sunscreens is between 0.5 and 15% by weight.

13. A process for protecting the human epidermis against UV rays, comprising applying an effective amount of the composition of claim 5 to the skin.

* * * * *